(12) United States Patent
Kamei et al.

(10) Patent No.: US 7,821,644 B2
(45) Date of Patent: Oct. 26, 2010

(54) APPARATUS FOR VISUAL INSPECTION (75) Inventors: Mitsuhiro Kamei, Takahagi (JP); Kei Shimura, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 362 days.

(21) Appl. No.: 11/262,826

(22) Filed: Nov. 1, 2005

(65) Prior Publication Data
US 2006/0092426 A1 May 4, 2006

(30) Foreign Application Priority Data
Nov. 4, 2004 (JP) .............................. 2004-320771

(51) Int. Cl.
G01B 9/02 (2006.01)
(52) U.S. Cl. .................................... 356/491; 356/237.2
(58) Field of Classification Search ................. 356/495, 356/490, 489, 508, 511–514
See application file for complete search history.

(56) References Cited
U.S. PATENT DOCUMENTS

| 6,999,183 | B2 * | 2/2006 | Nielsen et al. ............... 356/612 |
| 7,145,661 | B2 * | 12/2006 | Hitzenberger ............... 356/497 |
| 7,251,024 | B2 * | 7/2007 | Maeda et al. ............. 356/237.2 |
| 2004/0115843 | A1 * | 6/2004 | Wack et al. .................... 438/14 |
| 2004/0150821 | A1 * | 8/2004 | Shibata et al. .............. 356/369 |
| 2006/0082781 | A1 * | 4/2006 | Chan et al. .................. 356/495 |

FOREIGN PATENT DOCUMENTS

| JP | 61-104243 | 5/1986 |
| JP | 2000-155099 | 6/2000 |
| JP | 2002-039960 | 2/2002 |
| JP | 2003-344306 | 12/2003 |

OTHER PUBLICATIONS

Japanese Office Action, w/ English translation thereof, issued in Japanese Patent Application No. JP 2004-320771 drafted Nov. 16, 2009.

* cited by examiner

*Primary Examiner*—Tarifur Chowdhury
*Assistant Examiner*—Jonathan M Hansen
(74) *Attorney, Agent, or Firm*—McDermott Will & Emery LLP (57) ABSTRACT

An apparatus is provided which reduces the dependency of the direction of polarization on channels of an image sensor so as to improve the sensitivity of inspection. In the apparatus, the direction of an illumination beam incident on a polarizing beam splitter is made to be substantially parallel to the longitudinal direction of a field of view of an image sensor projected on the polarizing beam splitter.

9 Claims, 7 Drawing Sheets

APPARATUS FOR VISUAL INSPECTION

BACKGROUND OF THE INVENTION

The present invention relates to an apparatus for visual inspection adapted to detect defects of a pattern to be inspected and more particularly, to a visual inspection apparatus used for inspecting pattern defects and foreign particles in the course of production of a semiconductor wafer, a photomask, a printed circuit board and so on.

Figure 4:
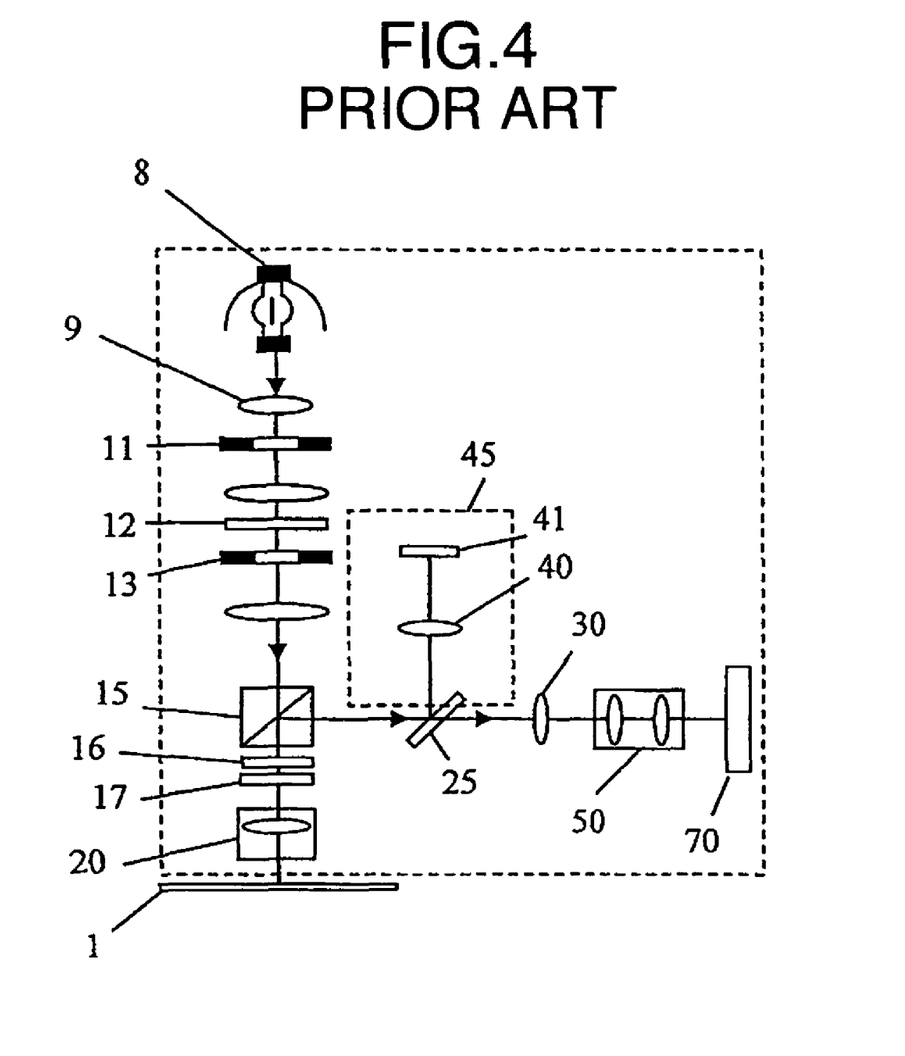
FIG. 4 is a diagram showing an example of construction of an optical system of conventional visual inspection apparatus.

In visual inspection of a semiconductor wafer, a method is known as disclosed in, for examples JP-A-2000-155099, according to which when an illumination beam of rays of light is reflected on the surface of a specimen and an optical image of the specimen is formed by interference of a zero-order diffraction ray and higher-order diffraction rays of a reflected beam, the contrast of the optical image is improved to detect a defect of a fine wiring pattern formed on the specimen with high sensitivity. A basic construction of an optical system used for the method is shown in FIG. 4. A beam of light emitted from a light source 8 reaches an aperture stop 11 through a concave mirror and lens 9 and then is rendered to be incident on a polarizing beam splitter 15 by way of a lens, a band-pass filter 12 and a field stop 13. The beam transmits through the polarizing beam splitter 15 and a resultant linearly polarized light beam leaving the splitter passes through a half waveplate 16 and a quarter waveplate 17 so as to be converted into an elliptically polarized light which in turn is irradiated on a specimen 1 by means of an objective lens 20. The direction of major axis of the elliptically polarized light can be controlled by rotating the quarter waveplate 17 and the ellipticity of the elliptically polarized light can be controlled by rotating the half waveplate 16. A beam of light reflected from the specimen 1 also enters the polarizing beam splitter 15 via the objective lens 20, quarter waveplate 17 and half waveplate 16 and then only an S-polarised component is reflected and led to an imaging optics comprised of an imaging lens 30 and a zoom lens 50. The optical image of the specimen 1 is formed on an image sensor 70. Then the image is converted to image data and defects are detected by processing the image data.

When, in this imaging optics, angles of the two waveplates are settled such that the specimen 1 is illuminated with a circularly polarized light, only a component having its polarization state unchanged during the reflection on the specimen surface is reflected at the polarizing beam splitter 15 and led to the imaging optics. On the other hand, when angles of the two waveplates are settled such that the specimen 1 is illuminated with an elliptically polarized light, part of a component having its polarization state changed during the reflection on the specimen 1 is also reflected at the polarizing beam splitter 15 and led to the imaging optics. Generally speaking, a beam of light rays diffracted by a linear pattern sometimes changes its polarization state but a zero-order ray does not change its polarization state. Accordingly, by illuminating the elliptically polarized light, the diffracted light component can be emphasized and then led to the imaging optics.

Hereinafter, the degree of emphasis of a diffracted beam attributable to the elliptically polarized light illumination will be called an SR intensity. The image sensor 70 is constructed of groups of pixels and typically, individual groups are called channels. For example, all the pixels on the sensor are divided into 32 or 64 channels.

The SR intensity has dependency on channels of the image sensor. Accordingly, under one illumination condition, the sensitivity differs between channels and therefore the condition is settled by a value of average sensitivity. In order to improve the inspection sensitivity, the difference in sensitivity between channels of the image sensor needs to be reduced.

An object of the present invention is to realize an optical system capable of improving the inspection sensitivity by reducing the dependency of the SR intensity upon channels on the image sensor.

SUMMARY OF THE INVENTION

Figure 3A:
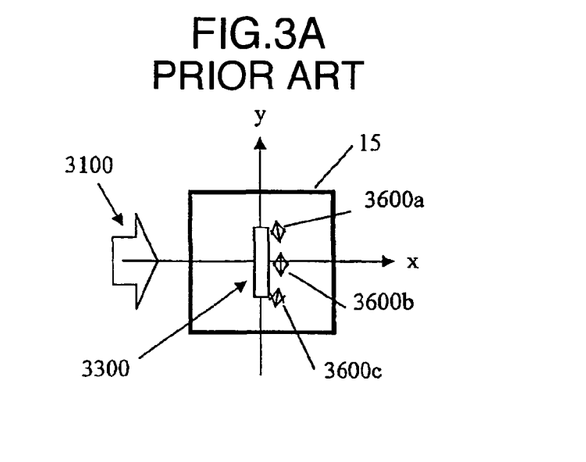
FIG. 3A is a top view showing an optical system layout according to the prior art.
Figure 3B:
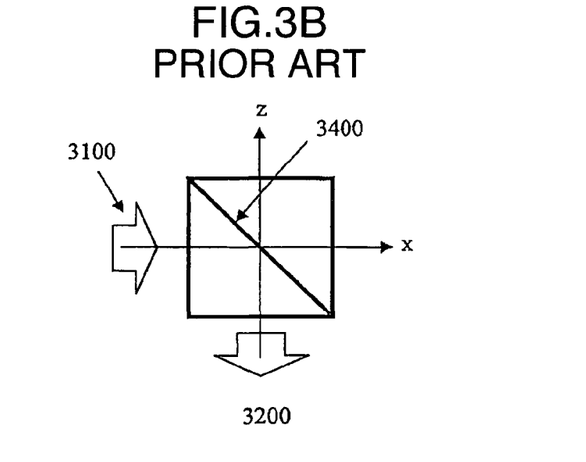
FIG. 3B is a side view showing an optical system layout according to the prior art.

It has been found out that the direction of incidence of an incident light on the polarizing beam splitter has relation to the dependency of the SR intensity upon channels. FIGS. 3A and 3B are useful to explain how the direction of the incident light, the reflection surface of polarizing beam splitter and the shape of a field of view of image sensor projected on the polarizing beam splitter are related to one another in the conventional visual inspection apparatus. The direction of an incident illumination light 3100 is substantially vertical to the longitudinal direction of the field of view of the image sensor, 3300, which is projected on the polarizing beam splitter 15. Because of the substantial verticalness of the direction of the incident light to the longitudinal direction of the field of view of image sensor projected on the polarizing beam splitter, the incident angle shifts more largely at longitudinal ends than in the center portion and the direction of polarization of the reflected illumination light beam shifts. Since the longitudinal direction of oblong shape of the image sensor corresponds to the channel direction of the aforementioned 1 to 32 or 1 to 64 channels, the dependency on channels is caused as described previously.

In the present invention, an optical system arrangement is adopted in which the direction of an incident light beam on the polarizing beam splitter is so adjusted as to be substantially parallel to the longitudinal direction of a substantially oblong-shaped view field of the image sensor projected on the polarizing beam splitter.

According to the present invention, since the dependency of the direction of polarization on channels of the image sensor can be reduced, the polarization direction can be optimized easily and a reduction in sensitivity depending on channels can be obviated, with the result that the defect detection sensitivity can be improved as a whole.

Other objects, features and advantages of the invention will become apparent from the following description of the embodiments of the invention taken in conjunction with the accompanying drawings.

DESCRIPTION OF THE EMBODIMENTS

Embodiments of the present invention will now be described with reference to the accompanying drawings.

Figure 1:
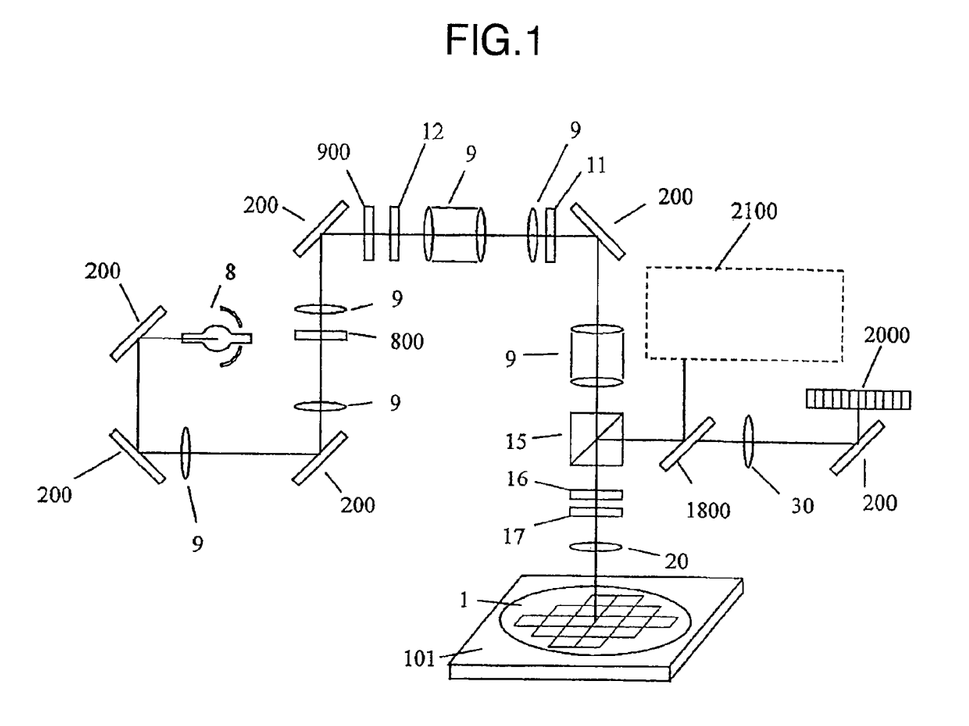
FIG. 1 is a schematic diagram showing an embodiment of a visual inspection apparatus according to the present invention.

In an embodiment of an apparatus for visual inspection according to the present invention as schematically illustrated in FIG. 1, a specimen 1 is chucked on a stage 101 and is movable to optimum positions as necessary in rotating direction, X direction, Y direction and height direction, respectively. A beam of light rays emitted from a light source 8 reaches a polarizing beam splitter 15 by way of midway mirror 200, sharp-cut filter 300, lens 9, cone lens 700, diffuser 800, ND filter 900, band-pass filter 12 and opening of aperture stop 11. The beam transmits through the filter and a resultant linearly polarized light leaving the polarizing beam splitter 15 travels through a half waveplate 16 and a quarter waveplate 17 so as to be converted into an elliptically polarized light which in turn is irradiated on the specimen 1 by means of an objective lens 20. The direction of major axis of the elliptical polarization can be controlled by rotating the quarter waveplate 17 and the ellipticity of the elliptical polarization can be controlled by rotating the half waveplate 16.

A beam of light reflected from the specimen 1 enters the polarizing beam splitter 15 via the objective lens 20, quarter waveplate 17 and half waveplate 16 and only an S-polarized component is reflected, thus traveling through an imaging lens 30 to form an image of the specimen 1 on the light receiving surface of an image sensor 2000. Used as the image sensor 2000 is, for example, a linear sensor or a TDI image sensor. Part of the light beam reflected from the specimen 1 and then reflected from the polarizing beam splitter 15 is separated by means of a beam splitter 1800 and led to an auto-focus system 2100, being used for controlling the specimen in the height direction.

A mercury lamp or a xenon lamp may be used as the light source 8 but with a laser beam source used, a highly intensive photo-output can be obtained in the DUV (Deep Ultra Violet) range.

The image sensor 2000 referred to herein is a TDI image sensor having its light receiving surface constructed of 256× 4096 CCD's and taking a rectangular form sized to 3.3 mm×53.2 mm. Further, in the direction of 4096 pixels, the 4096 pixels are divided into, for example, 64 channels. Accordingly, in the present embodiment, the TDI image sensor has 64 channels in the longitudinal direction of the rectangular form. In FIG. 1, the image sensor 2000 is arranged in such a manner that its longitudinal direction coincides with the right and left direction on the sheet of drawing and therefore, the image sensor has its field of view, which is projected on the polarizing beam splitter 15, in the horizontal direction on the sheet of drawing. Since the direction of optical path from the polarizing beam splitter 15 toward the imaging optics is horizontal on the sheet of drawing in the FIG. 1, these directions coincide with each other.

Figure 2A:
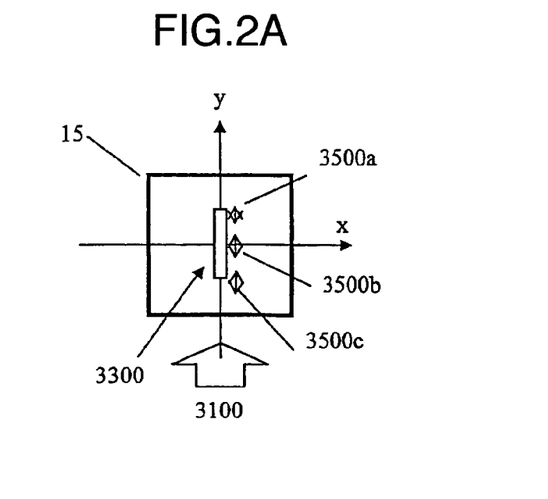
FIG. 2A is a top view showing an example of an optical system layout according to the invention in top view form.
Figure 2B:
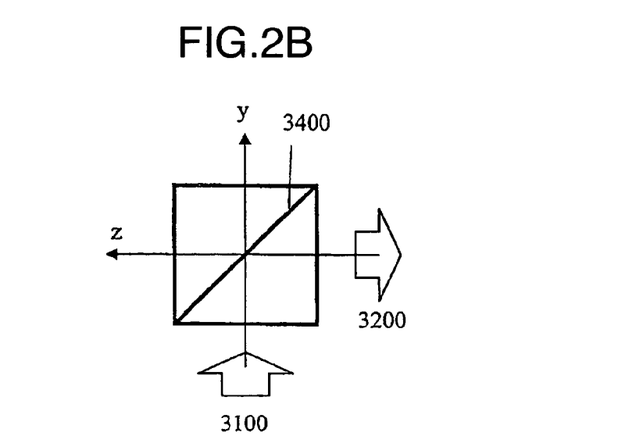
FIG. 2B is a side view showing an example of an optical system layout according to the invention.

In the visual inspection apparatus of the invention, the polarizing beam splitter, image sensor view field shape, incident beam and reflection beam are related to one another as schematically illustrated in FIGS. 2A and 2B. In the prior art, like relationship is held as schematically illustrated in FIGS. 3A and 3B. FIGS. 2A and 3A are top views and FIGS. 2B and 3B are side views. Effects of the present invention will be described by making reference to these Figures.

Figure 3C:
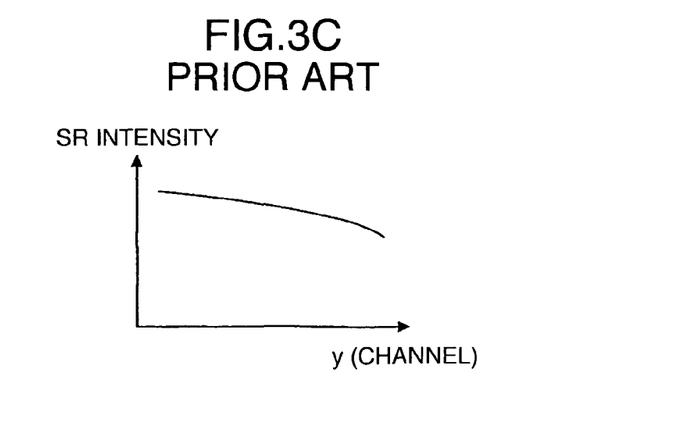
FIG. 3C is a graph for explaining effect of the conventional optical system layout.

Firstly, the conventional optical system will be described. In FIG. 3A, an incident light beam 3100 enters the polarizing beam splitter 15 horizontally in the left to right direction. As illustrated, the image sensor view field 3300 projected on the polarizing beam splitter 15 has its longitudinal direction (channel direction) coincident with the vertical direction. A reflection surface 3400 of the polarizing beam splitter is related to a reflection beam 3200 as shown in FIG. 3B. FIG. 3A shows a direction of polarization in the central part of the image sensor view field, 3600$b$, and directions of polarization at the ends of the image sensor view field, 3600$a$ and 3600$c$. Incident light rays reaching the individual positions (individual channels) of the image sensor view field have been incident on the reflection surface 3400 at different angles, so that the polarization directions 3600$a$, 3600$b$ and 3600$c$ differ slightly from one another. As the result, the dependency of SR intensity on channels of the image sensor occurs as shown in FIG. 3C.

Figure 2C:
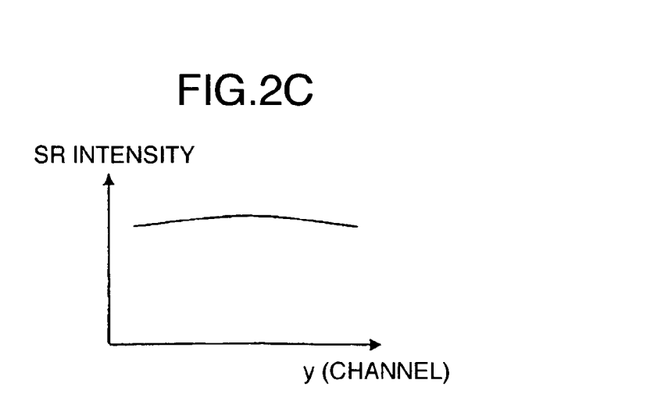
FIG. 2C is a graph for explaining effect of the optical system layout.

Next, an optical system of the present invention will be described. In an layout of the invention as shown in FIG. 2A, the longitudinal direction (channel direction) of an image sensor view field 3300 projected on the polarizing beam splitter 15 coincides with the direction of an incident illumination light beam 3100. With this construction, incident light rays reaching the individual positions (individual channels) of the image sensor view field have been incident on a reflection surface 3400 at the same incident angle, so that the polarization directions 3500$b$, 3500$a$ and 3500$c$ in the center and at the opposite ends of the image sensor view field, respectively, are identical with one another. As the result, the dependency of SR intensity on channels of the image sensor does not occur as shown in FIG. 2C.

Figure 7:
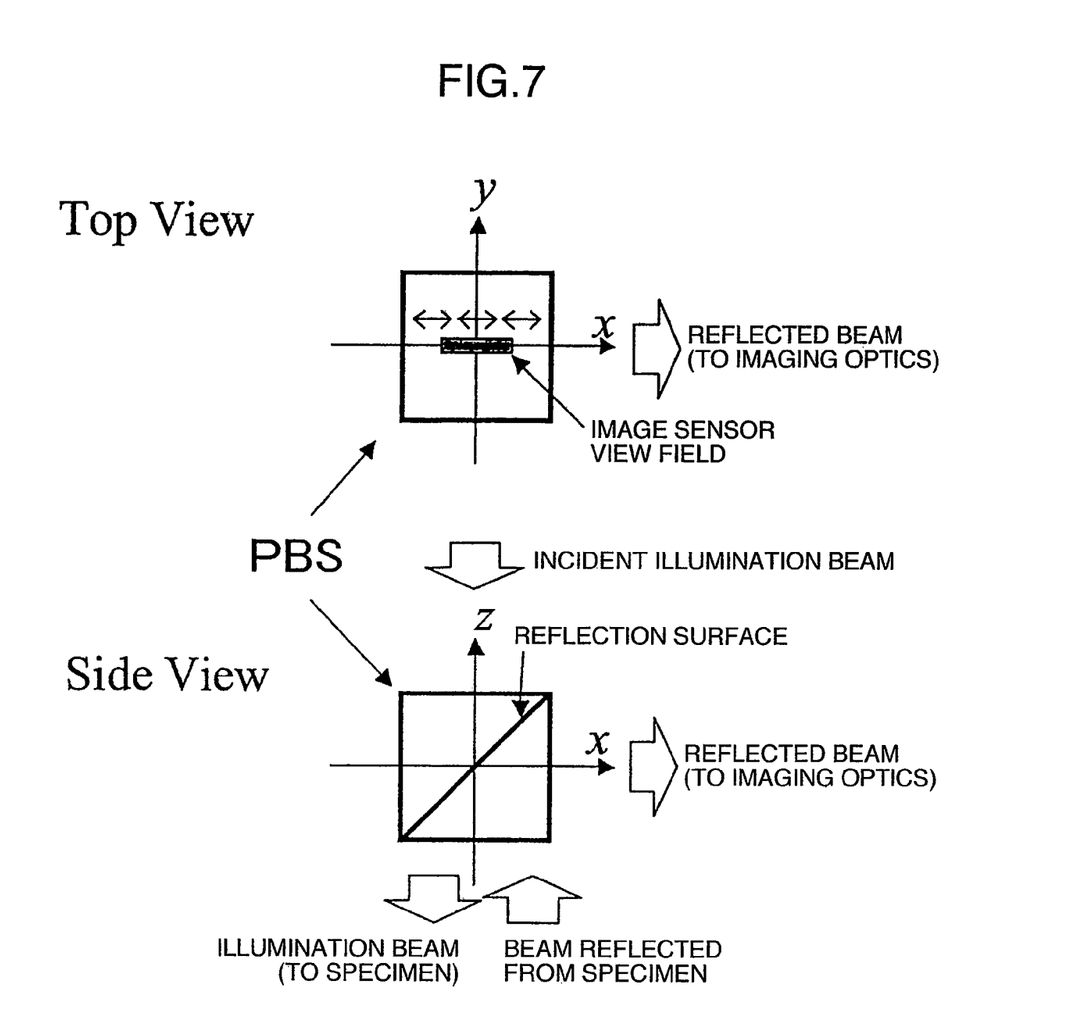
FIG. 7 is a diagram showing another example of the optical system layout according to the invention.

Another example of the optical system according to the invention is illustrated in FIG. 7. In this example, an illumination light beam from the light source enters the polarizing beam splitter from above and a beam transmitting through it illuminates the specimen. A reflected beam from the specimen is reflected at the reflection surface of the polarizing beam splitter and led to the imaging optics. In this layout, the longitudinal direction (channel direction) of image sensor view field projected on the polarizing beam splitter is substantially parallel to an optical path extending from the polarizing beam splitter and ending in the imaging optics. With this construction, an illumination light ray illuminating the center of the image sensor view field and illumination light rays illuminating the opposite ends thereof have the same incident surface in relation to the reflection surface of the polarizing beam splitter, thereby ensuring that polarization directions of these illumination light rays on the image sensor view field can all be parallel to the longitudinal direction of the image sensor view field. As a result, the illumination characteristics have no dependency upon channels of the image sensor and the SR intensity does not sustain the dependency on channels.

Figure 5:
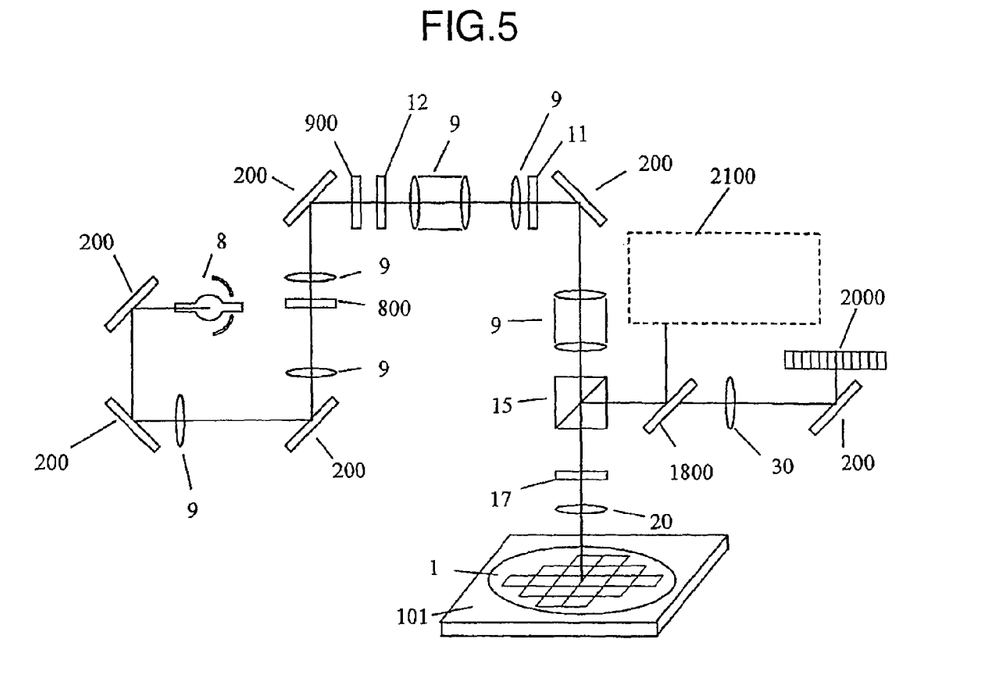
FIG. 5 is a schematic diagram showing another embodiment of the visual inspection apparatus according to the invention.

Another embodiment of the visual inspection apparatus according to the invention is schematically illustrated in FIG. 5. The apparatus shown in FIG. 5 differs from the visual inspection apparatus shown in FIG. 1 having the half waveplate 16 and quarter waveplate 17 arranged between the polarizing beam splitter 15 and objective lens 20 in that only a quarter waveplate 17 is interposed. The visual inspection apparatus constructed as shown in FIG. 1 is suitable for use with illumination by an elliptically polarized beam but the apparatus constructed as shown in FIG. 5 is effective when a circularly polarized beam is used for illumination.

Figure 6:
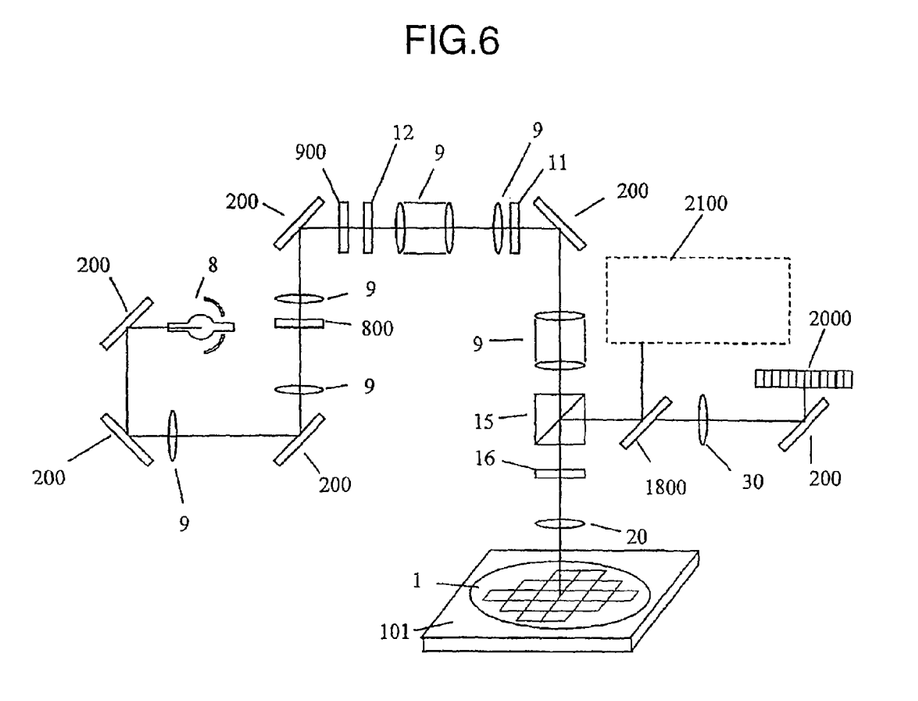
FIG. 6 is a schematic diagram showing still another embodiment of the visual inspection apparatus according to the invention.

Still another embodiment of the visual inspection apparatus according to the invention is schematically illustrated in FIG. 6. The apparatus shown in FIG. 6 is also identical to the visual inspection apparatus having the half waveplate 16 and quarter waveplate 17 arranged between the polarizing beam splitter 15 and objective lens 20, with the only exception that a half waveplate 16 alone is interposed. This visual inspection apparatus is effective when a linearly polarized beam is used for illumination.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus for inspecting a specimen with patterns formed thereon comprising:
   a specimen stage for holding said specimen;
   a light source;
   an illumination optic for illuminating an area on said specimen with said light source;
   a diffuser;
   a polarizing beam splitter;
   an objective lens;
   a quarter waveplate arranged between said polarizing beam splitter and said objective lens;
   an imaging optic for forming an image of said specimen; and
   a photoelectric conversion image sensor for obtaining images of a part of said illuminated area on said specimen, comprising an array of channels in a longitudinal direction, each channel comprising pixels,
   wherein an illumination beam of light rays emitted from said light source is irradiated on the specimen held by said specimen stage via said diffuser, said polarizing beam splitter, said quarter waveplate and said objective lens,
   wherein a reflection beam from said specimen is led to said imaging optic by way of said objective lens, quarter waveplate and polarizing beam splitter so as to image said specimen on said image sensor, and
   wherein the direction of the illumination beam from said light source incident on said polarizing beam splitter is substantially parallel to said longitudinal direction of said array of channels of said photoelectric conversion image sensor projected on said polarizing beam splitter, and
   polarization directions in the center and at opposite ends of said photoelectric conversion image sensor view field, respectively, are identical with one another to reduce dependency of inspection sensitivity on channels of said photoelectric conversion image sensor so as to improve sensitivity of said inspection.

2. The inspection apparatus for inspecting a specimen with patterns formed thereon according to claim 1, wherein said light source is a laser beam source.

3. An inspection apparatus for inspecting a specimen with patterns formed thereon comprising,
   a specimen stage for holding a specimen;
   a light source;
   an illumination optic for illuminating an area on said specimen with said light source;
   a diffuser;
   a polarizing beam splitter;
   an objective lens;
   a half waveplate arranged between said polarizing beam splitter and objective lens;
   an imaging optic for forming an image of said specimen; and
   a photoelectric conversion image sensor for obtaining images of a part of said illuminated area on said specimen, comprising an array of channels in a longitudinal direction, each channel comprising pixels,
   wherein an illumination beam of light rays is emitted from said light source is irradiated on the specimen held by said specimen stage via said diffuser, said polarizing beam splitter, said half waveplate and said objective lens,
   wherein a reflection beam from said specimen is led to said imaging optic by way of said objective lens, half waveplate and polarizing beam splitter so as to image said specimen on said photoelectric conversion image sensor, and
   wherein the direction of the illumination beam from said light source incident on said polarizing beam splitter is substantially parallel to said longitudinal direction of said array of channels of said photoelectric conversion image sensor projected on said polarizing beam splitter, and
   polarization directions in the center and at opposite ends of said photoelectric conversion image sensor view field, respectively, are identical with one another to reduce dependency of inspection sensitivity on channels of said photoelectric conversion image sensor so as to improve sensitivity of said inspection.

4. The inspection apparatus for inspecting a specimen with patterns formed thereon according to claim 3, wherein said light source is a laser beam source.

5. An inspection apparatus for inspecting a specimen with patterns formed thereon comprising;
   a specimen stage for holding a specimen;
   a light source;
   an illumination optic for illuminating an area on said specimen with said light source;
   a diffuser;
   a polarizing beam splitter;
   an objective lens;
   a quarter waveplate arranged between said polarizing beam splitter and objective lens;
   a half waveplate arranged between said polarizing beam splitter and objective lens;
   an imaging optic for forming an image of said specimen; and
   a photoelectric conversion image sensor for obtaining images of a part of said illuminated area on said specimen, comprising an array of channels in a longitudinal direction, each channel comprising pixels,
   wherein an illumination beam from said light source is irradiated on the specimen held by said specimen stage via said diffuser, said polarizing beam splitter, said quarter waveplate, said half waveplate and said objective lens,
   wherein a reflection beam from said specimen is led to said imaging optic by way of said objective lens, a quarter waveplate, a half waveplate and polarizing beam splitter so as to image said specimen on said photoelectric conversion image sensor, and
   wherein the direction of the illumination beam from said light source incident on said polarizing beam splitter is substantially parallel to said longitudinal direction of said array of channels of said photoelectric conversion image sensor projected on said polarizing beam splitter, and polarization directions in the center and at opposite ends of said photoelectric conversion image sensor view field, respectively, are identical with one another to reduce dependency of inspection sensitivity on channels of said photoelectric conversion image sensor so as to improve sensitivity of said inspection.

6. The inspection apparatus for inspecting a specimen with patterns formed thereon according to claim 5, wherein said light source is a laser beam source.

7. A method for inspecting a specimen with patterns formed thereon with an inspection apparatus, the inspection apparatus comprising:
   a specimen stage for holding said specimen;
   a light source;
   an illumination optic for illuminating an area on said specimen with said light source;
   a diffuser;
   a polarizing beam splitter;
   an objective lens;
   a quarter waveplate arranged between said polarizing beam splitter and said objective lens;
   an imaging optic for forming an image of said specimen; and
   a photoelectric conversion image sensor for obtaining images of a part of said illuminated area on said specimen, comprising an array of channels in a longitudinal direction, each channel comprising pixels, comprising the steps of:
   illuminating an area on said specimen with said light source,
   obtaining images of a part of said illuminated area on said specimen with said photoelectric conversion image sensor,
   irradiating an illumination beam of light rays that are emitted from said light source on the specimen held by said specimen stage via said diffuser, said polarizing beam splitter, said quarter waveplate and said objective lens, and
   imaging said specimen on said image sensor by leading a reflection beam from said specimen to said imaging optic by way of said objective lens, quarter waveplate and polarizing beam splitter,
   wherein the direction of the illumination beam from said light source incident on said polarizing beam splitter is substantially parallel to said longitudinal direction of said array of channels of said photoelectric conversion image sensor projected on said polarizing beam splitter, and
   polarization directions in the center and at opposite ends of said photoelectric conversion image sensor view field, respectively, are identical with one another to reduce dependency of inspection sensitivity on channels of said photoelectric conversion image sensor so as to improve sensitivity of said inspection.

8. A method for inspecting a specimen with patterns formed thereon using an inspection apparatus, the inspection apparatus comprising,
   a specimen stage for holding a specimen;
   a light source;
   an illumination optic for illuminating an area on said specimen with said light source;
   a diffuser;
   a polarizing beam splitter;
   an objective lens;
   a half waveplate arranged between said polarizing beam splitter and objective lens;
   an imaging optic for forming an image of said specimen; and
   a photoelectric conversion image sensor for obtaining images of a part of said illuminated area on said specimen, comprising an array of channels in a longitudinal direction, each channel comprising pixels, comprising the steps of:
   illuminating an area on said specimen with said light source,
   obtaining images of a part of said illuminated area on said specimen with said photoelectric conversion image sensor,
   irradiating an illumination beam of light rays emitted from said light source on the specimen held by said specimen stage via said diffuser, said polarizing beam splitter, said half waveplate and said objective lens, and
   imaging said specimen on said photoelectric conversion image sensor by leading a reflection beam from said specimen to said imaging optic by way of said objective lens, half waveplate and polarizing beam splitter,
   wherein the direction of the illumination beam from said light source incident on said polarizing beam splitter is substantially parallel to said longitudinal direction of said array of channels of said photoelectric conversion image sensor projected on said polarizing beam splitter, and
   polarization directions in the center and at opposite ends of said photoelectric conversion image sensor view field, respectively, are identical with one another to reduce dependency of inspection sensitivity on channels of said photoelectric conversion image sensor so as to improve sensitivity of said inspection.

9. A method for inspecting a specimen with patterns formed thereon comprising:
   a specimen stage for holding a specimen;
   a light source;
   an illumination optic for illuminating an area on said specimen with said light source;
   a diffuser;
   a polarizing beam splitter;
   an objective lens;
   a quarter waveplate arranged between said polarizing beam splitter and objective lens;
   a half waveplate arranged between said polarizing beam splitter and objective lens;
   an imaging optic for forming an image of said specimen; and
   a photoelectric conversion image sensor for obtaining images of a part of said illuminated area on said specimen, comprising an array of channels in a longitudinal direction, each channel comprising pixels comprising the steps of:
   illuminating an area on said specimen with said light source,
   obtaining images of a part of said illuminated area on said specimen with said photoelectric conversion image sensor,
   irradiating an illumination beam of light rays emitted from said light source on the specimen held by said specimen stage via said diffuser, said polarizing beam splitter, said half waveplate and said objective lens, and imaging said specimen on said photoelectric conversion image sensor by leading a reflection beam from said specimen to said imaging optic by way of said objective lens, half waveplate and polarizing beam splitter, wherein the direction of the illumination beam from said light source incident on said polarizing beam splitter is substantially parallel to said longitudinal direction of said array of channels of said photoelectric conversion image sensor projected on said polarizing beam splitter, and polarization directions in the center and at opposite ends of said photoelectric conversion image sensor view field, respectively, are identical with one another to reduce dependency of inspection sensitivity on channels of said photoelectric conversion image sensor so as to improve sensitivity of said inspection.

* * * * *